(12) United States Patent
Hsieh

(10) Patent No.: US 11,019,726 B2
(45) Date of Patent: May 25, 2021

(54) LIGHT EMITTING DEVICE WITH EXTENDABLE AND FLEXIBLE CARRIER

(71) Applicant: EPISTAR CORPORATION, Hsinchu (TW)

(72) Inventor: Min-Hsun Hsieh, Hsinchu (TW)

(73) Assignee: Epistar Corporation, Hsinchu (TW)

( * ) Notice: Subject to any disclaimer, the term of this patent is extended or adjusted under 35 U.S.C. 154(b) by 0 days.

(21) Appl. No.: 16/451,832

(22) Filed: Jun. 25, 2019

(65) Prior Publication Data

US 2019/0394879 A1 Dec. 26, 2019

(30) Foreign Application Priority Data

Jun. 25, 2018 (TW) ................................ 107121654

(51) Int. Cl.
*H05K 1/00* (2006.01)
*H05K 1/18* (2006.01)
*H01L 33/62* (2010.01)
*A61N 5/06* (2006.01)

(52) U.S. Cl.
CPC ............. *H05K 1/189* (2013.01); *A61N 5/062* (2013.01); *H01L 33/62* (2013.01); *H05K 2201/10106* (2013.01); *H05K 2201/10287* (2013.01)

(58) Field of Classification Search
USPC ........................................................ 361/749
See application file for complete search history.

(56) References Cited

U.S. PATENT DOCUMENTS

| | | | |
|---|---|---|---|
| 2015/0246241 A1* | 9/2015 | Ho | A61N 5/0619 601/15 |
| 2016/0036142 A1* | 2/2016 | Mason | H01R 12/777 439/66 |
| 2016/0341415 A1* | 11/2016 | Lumaye | F21V 33/0004 |
| 2018/0043178 A1* | 2/2018 | Iguchi | A61N 5/062 |

* cited by examiner

*Primary Examiner* — Andargie M Aychillhum
(74) *Attorney, Agent, or Firm* — Muncy, Geissler, Olds & Lowe, P.C.

(57) ABSTRACT

A light-emitting device comprises a flexible carrier having a plurality of segmentations, a light-emitting unit and a connecting wire. The flexible carrier has a carrier part and an extendable part. The light-emitting unit is set on the carrier part. The extendable part has a plurality of segmentations. The flexible carrier has a continuous common surface.

19 Claims, 13 Drawing Sheets

# LIGHT EMITTING DEVICE WITH EXTENDABLE AND FLEXIBLE CARRIER

CROSS-REFERENCE TO RELATED APPLICATION

This application claims the benefit of Taiwan Patent Application No. 107121654, filed on Jun. 25, 2018, in the Taiwan Intellectual Property Office the disclosure of which is incorporated herein by reference in its entirety.

FIELD OF THE DISCLOSURE

The present disclosure relates to a light-emitting device, and more particularly to a light-emitting device that has an extendable and flexible carrier.

BACKGROUND OF THE DISCLOSURE

A light sheet is usually made by fixing LED packages on a circuit board through the surface-mount technology (SMT). For flexible electronics applications, the circuit board is made of a flexible material. When the circuit board is bended, there may be problems as follows:
1. Since the bending range of the connecting wires is less than the range of the circuit board, the connecting wires are possibly broken while the bending angle is over the limit. As a result, the effect of electrical connection is lost.
2. During bending, LED packages may be damage because the size of LED packages is too big.
3. LED packages are fixed on the circuit board only by solders, which might be loosened during bending and disconnect the electrical connection.

SUMMARY OF THE DISCLOSURE

A light-emitting device in accordance with an embodiment of the present disclosure comprises a flexible carrier, a light-emitting unit, a connecting wire, and a plurality of segmentations. The light-emitting unit and the connecting wire are set on the flexible carrier. The segmentations are formed within the flexible carrier. The flexible carrier has a continuous common surface.

BRIEF DESCRIPTION OF THE DRAWINGS

The structure and the technical means adopted by the present disclosure to achieve the above and other objects can be best understood by referring to the following detailed description of the embodiments and the accompanying drawings, wherein.

DETAILED DESCRIPTION OF THE EMBODIMENTS

Figure 1A:
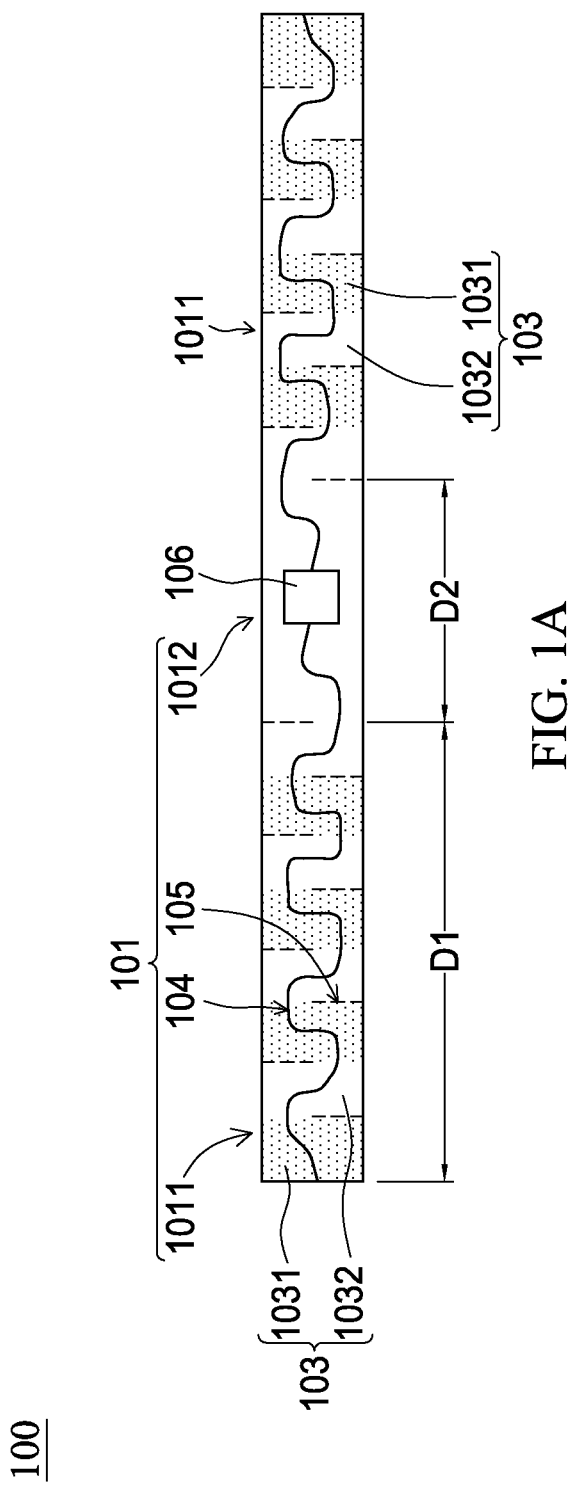
FIG. 1A is the top view of an extendable and flexible carrier of light-emitting device in accordance with a first embodiment of the present disclosure.

The present disclosure will now be described with some embodiments thereof and with reference to the accompanying drawings. Elements that are the same in the embodiments are denoted by the same reference numerals.

Figure 1B:
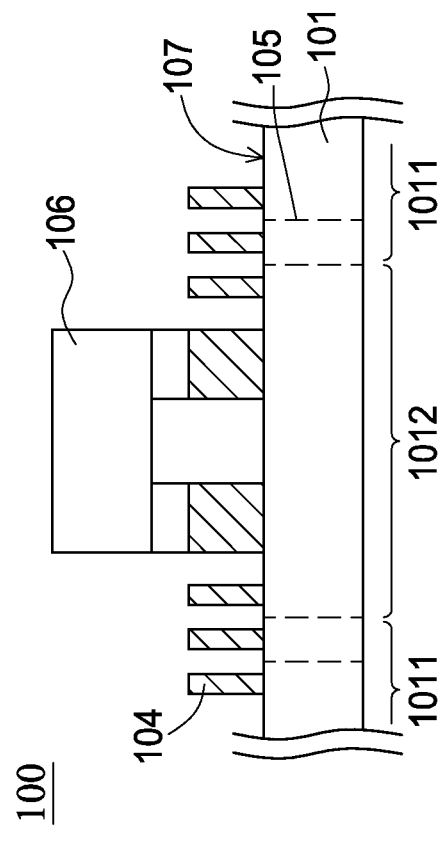
FIG. 1B is the side view of the light-emitting unit disclosed in FIG. 1A of the present disclosure.

FIG. 1A shows a top view of an extendable and flexible carrier of light-emitting device disclosed in a first embodiment of the present disclosure. A light-emitting device 100 has a flexible carrier 101. The flexible carrier 101 further comprises an extendable part 1011 and a carrier part 1012. The carrier part 1012 is marked as D2 in the FIG. 1A, and the remaining part of the flexible carrier 101 is the extendable part 1011. A light-emitting unit 106 is set on the carrier part 1012. A connecting wire 104 is set on the carrier part 1012 and flexible carrier 101 for electrically connecting the light-emitting unit 106 to other electronic devices electrically. The connecting wire 104 is a curved structure. The extendable part 1011 comprises a plurality of sub-carriers 103 and a plurality of segmentations 105 formed inside the flexible carrier 101. Each of the sub-carriers 103 comprises a first sub-carrier 1031 and a second sub-carrier 1032 respectively formed at two sides of each of the segmentations 105. Before the light-emitting device 100 is extended, the extendable part 1011 has a length D1 and the carrier part 1012 has a length D2. FIG. 1B shows, the side view of the light-emitting unit 106 disclosed in FIG. 1A, before the light-emitting device 100 is extended, the first sub-carrier 1031 and the second sub-carrier 1032 are close to each other to form a common surface 107, which is continuous and coplanar, with the carrier part 1012. In one embodiment, the common surface 107 is substantially a surface having one plane.

Figure 2A:
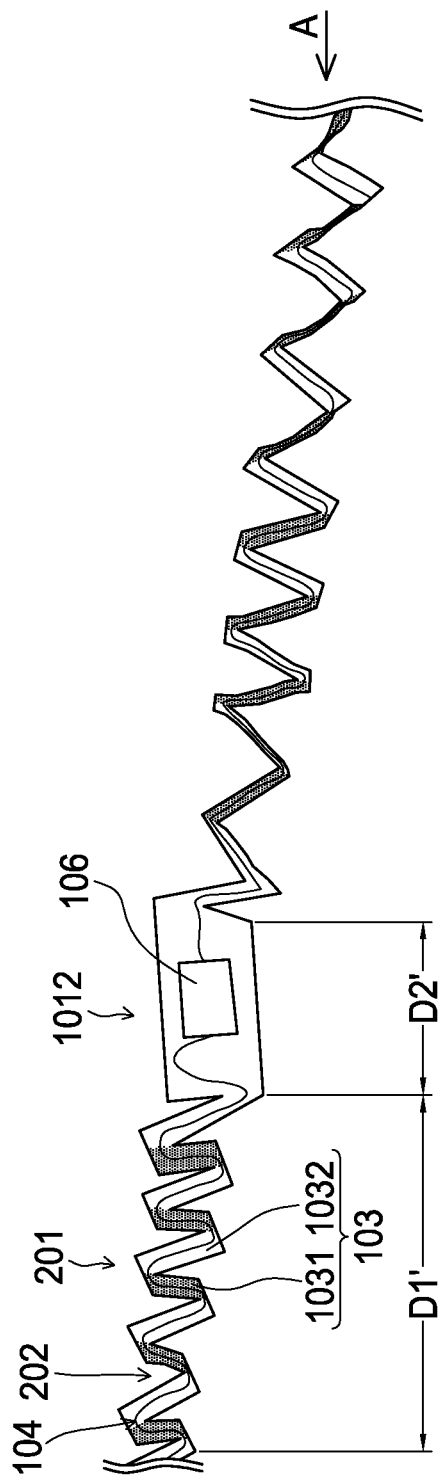
FIG. 2A shows the top view of the light-emitting device disclosed in FIG. 1A of the present disclosure after being extended.
Figure 2B:
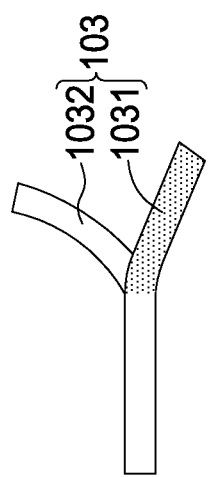
FIG. 2B shows the side view of the flexible carrier along the direction indicted by an arrow shown in FIG. 2A.

FIG. 2A shows the top view of the light-emitting device disclosed in FIG. 1A after being extended, the light-emitting device 100 has an extending part 201 and a carrier part 1012. The extending part 201 has a length D1' and the carrier part 1012 has a length D2' after the light-emitting device 100 is extended. The length D1' is larger than the length D1, and the length D2' is equal to the length D2. The extending part 201 comprises a plurality of sub-carriers 103 and a connecting wire 104. Each of the sub-carriers 103 comprises a first sub-carrier 1031 and a second sub-carrier 1032. After the light-emitting device 100 is extended, the first sub-carrier 1031 and the second sub-carrier 1032 are just partially close to each other, which results in a gap 202 being formed between the first sub-carrier 1031 and the second sub-carrier 1032. At this point, the first sub-carrier 1031 and the second sub-carrier 1032 do not form a common surface 107 with the carrier part 1012 anymore. In one embodiment, after the light-emitting device 100 being extended, the first sub-carrier 1031 and the second sub-carrier 1032 shift in a direction opposite to each other. In detail, as FIG. 2B, viewing from the side view of the flexible carrier indicated by an arrow A shown in FIG. 2A, FIG. 2B shows the first sub-carrier 1031 shifts downward and the second sub-carrier 1032 shifts upward, so that the first sub-carrier 1031 and the second sub-carrier 1032 become two segments with different planes or heights to each other In other words, the structure of the sub-carriers 103 develops from a structure with a single plane structure to a structure with two segments having different planes or heights to each other.

Figure 3A:
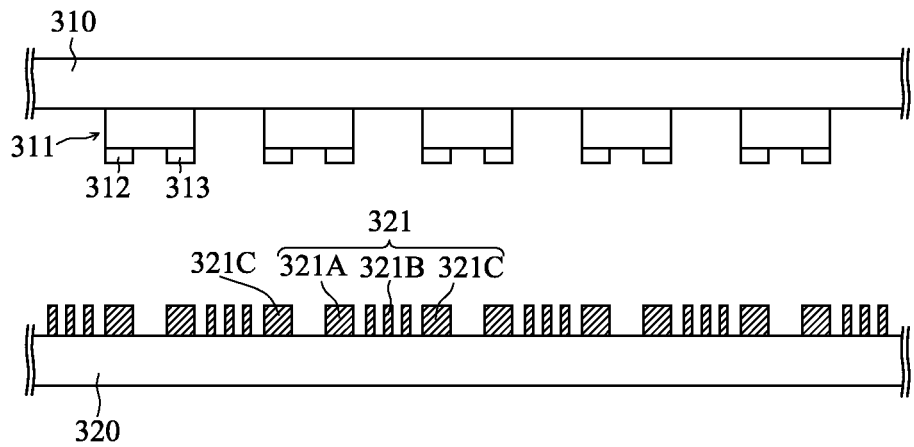
FIGS. 3A-3C show the cross-sectional views of manufacturing process of the light-emitting device in accordance with one embodiment of the present disclosure.
Figure 3B:
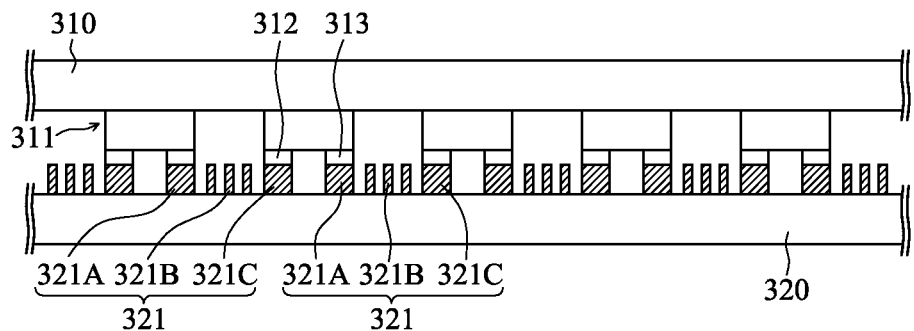
Figure 3C:
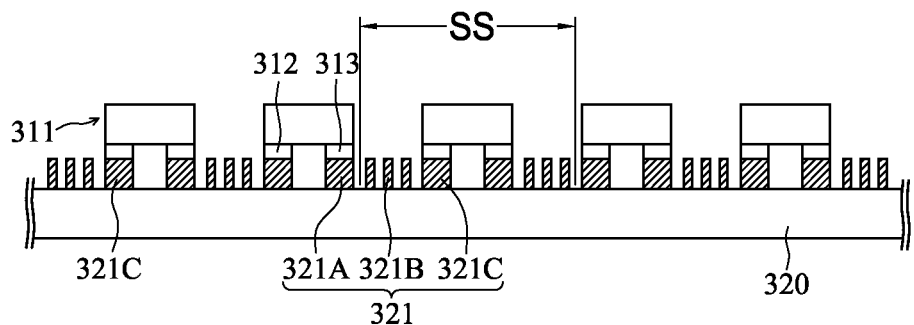
Figure 3D:
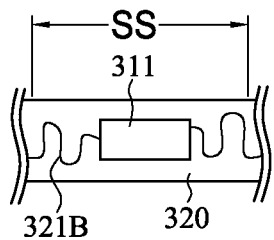
FIG. 3D shows the top view of the SS area of the light-emitting device disclosed in FIG. 3C.
Figure 3E:
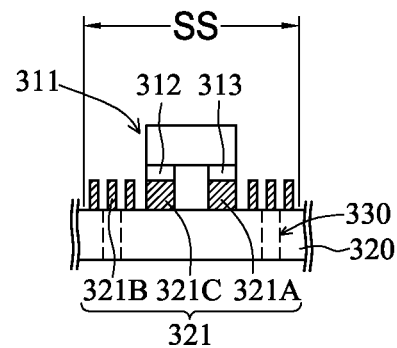
FIG. 3E shows the top view of partial area of the light-emitting device having segmentations in accordance with one embodiment of the present disclosure.
Figure 3E:
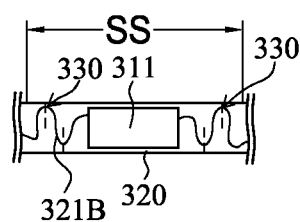

FIGS. 3A to 3C show the cross-sectional views of manufacturing process of the light-emitting device in accordance with one embodiment of the present disclosure. FIG. 3D shows the top view of a partial area of the light-emitting device 100. FIG. 3E shows the side view and the top view of a partial area of the light-emitting device 100 after being cut. FIG. 3A shows, a plurality of light-emitting units 311 set on the first carrier 310. Each of the light-emitting units 311 is a flip chip. In another embodiment, the light-emitting units 311 shown in FIG. 3A is a LED package. Each of the light-emitting units 311 includes a first pad 312, for example, a p-pad; and a second pad 313, for example, an n-pad. The first carrier 310 may include a temporary substrate, for example, a blue tape, a heat-dissipating sheet, a heat-dissipating gum, a UV releasing tape, or an adhesive layer, for connecting the light-emitting units 311 temporarily. The foregoing heat-dissipating sheet may be made of metal, ceramics, or graphite. The foregoing heat-dissipating gum may be epoxy resin or thermal conductive rubber. The foregoing adhesive layer may be a PET membrane.

A second carrier 320 including a plurality of conductive structures 321 thereon is provided. The second carrier 320 may be a flexible carrier. The second carrier 320 may be made of polymer, for example, polyimide.

Referring to FIG. 3A, each of those conductive structures 321 has a first connecting pad 321A, a second connecting pad 321C, and a connecting part 321B. The connecting part 321B is set between the first connecting pad 321A and the second connecting pad 321C. Each of the conductive structures 321 is separated from each other. In other words, the first connecting pad 321A of one of the conductive structures 321 is separated from the second connecting pad 321C of the other one of the adjacent conductive structures 321 with a space.

FIG. 3B shows, conductive structures 321 are connected to the light-emitting units 311. More specifically, each first pad 312 of each of the light-emitting units 311 physically connects to each second connecting pad 321C of each of the conductive structures 321; each second pad 313 of each of light-emitting units 311 physically connects to each first connecting pad 321A of each of the conductive structures 321, as a result, the light-emitting units 311 are fixed and connected electronically to the conductive structures 321. In this embodiment, each of the light-emitting units 311 is in series and connects electronically to the other one. In addition, one of the light-emitting units 311 is connected to two of the conductive structures 321, or, one of the conductive structures 321 is as a bridge joint between two of the light-emitting units 311. The first connecting pad 321A and the second connecting pad 321C may be eutectic bonding to the first pad 312 and the second pad 313, for example, forming an eutectic alloy; or, may be solder bonding to each other, for instance, forming an intermetallic compound to the first pad 312 and the second pad 313.

FIG. 3C shows, next, the first carrier 310 may be removed by dry etching, wet etching, laser lift-off, heating or UV light. FIG. 3D shows the top view corresponding to SS area of FIG. 3C, after removing the first carrier 310.

FIG. 3E shows, next, the second carrier 320 are cut into a plurality of segmentations 330, at this time, the manufacturing process of the light-emitting device 100 of the first embodiment is completed. In one another embodiment, the segmentations 330 may already be formed before the conductive structures 321 is connected to the light-emitting units 311. Next, making the conductive structures 321 connect to the light-emitting units 311, finally, the first carrier 310 is removed.

Figure 3F:
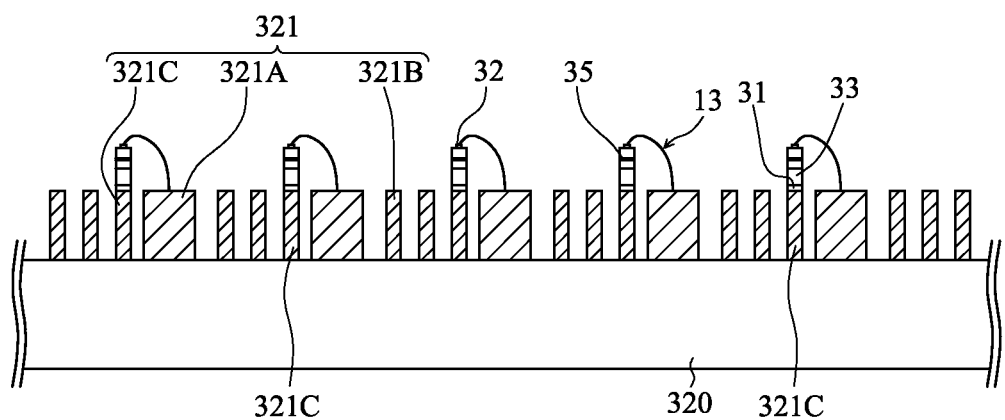
FIGS. 3F-3H show the side views of the light-emitting devices having different types of the light-emitting units in accordance with one another embodiment of the present disclosure.
Figure 3G:
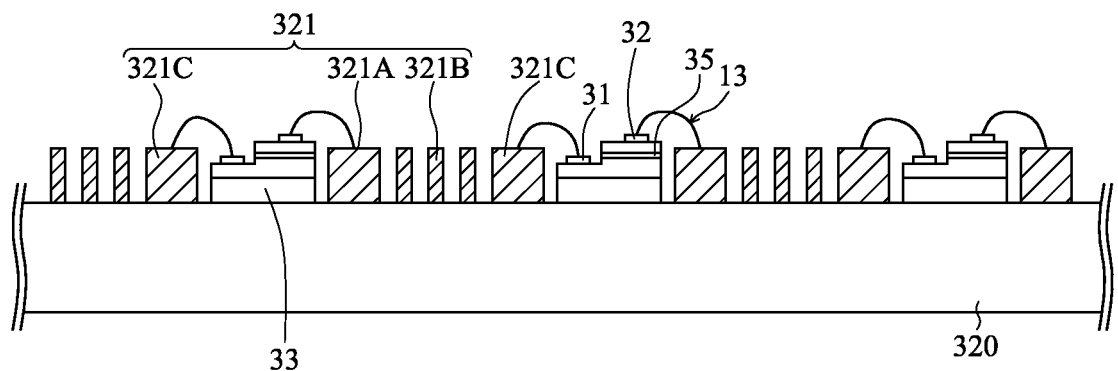
Figure 3H:
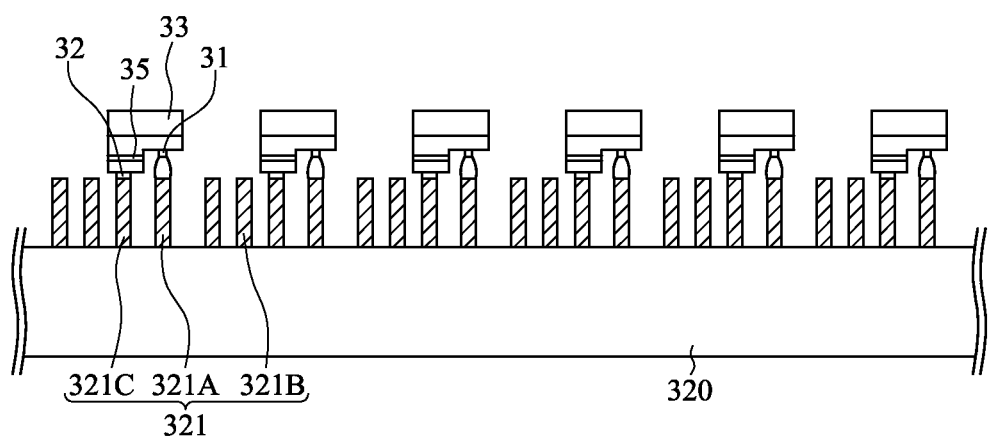

FIGS. 3F to 3H show the different types of the light-emitting units 311 in accordance with one embodiment of the present disclosure fixed to the second carrier.

FIG. 3F shows the light-emitting unit 311 in a vertical type LED chip. The light-emitting device 311 has two electrodes 31, 32, which are respectively at opposite sides of the active layer 350 of the light-emitting unit 311, and a substrate 33. The first electrode 31 is at the bottom of the light-emitting unit 311, fixed to the second carrier 320 by the material made of metal, such as Sn, Ag, Cu, Bi and so on, and connected to the second connecting pad 321C through a welding part (not showed in FIG. 3F). The second electrode 32 is at the top of the light-emitting unit 311 and connected to the first connecting pad 321A through a connecting wire 13.

FIG. 3G shows the light-emitting unit 311 in a horizontal type LED chip. The light-emitting unit 311 has two electrodes 31, 32 both at one the same side of the active layer 350 of the light-emitting unit 311. The electrodes 31, 32 are respectively connected electronically to the first connecting pad 321A and the second connecting pad 321C through the connecting wire 13. The bottom side of the light-emitting unit 311 is fixed to the second carrier 320 by thermal conduction material (not showed in FIG. 3G). The light-emitting device 311 in FIG. 3H is a horizontal type LED chip. The light-emitting unit 311 has two electrodes 31, 32 both at one the same side of the active layer 350 of the light-emitting unit 311. The light-emitting unit 311 is flipped and connected to the first connecting pad 321A and the second connecting pad 321C on the second carrier 320 through the material made of metal, such as Sn, Ag, Cu, Bi and so on.

Figure 4A:
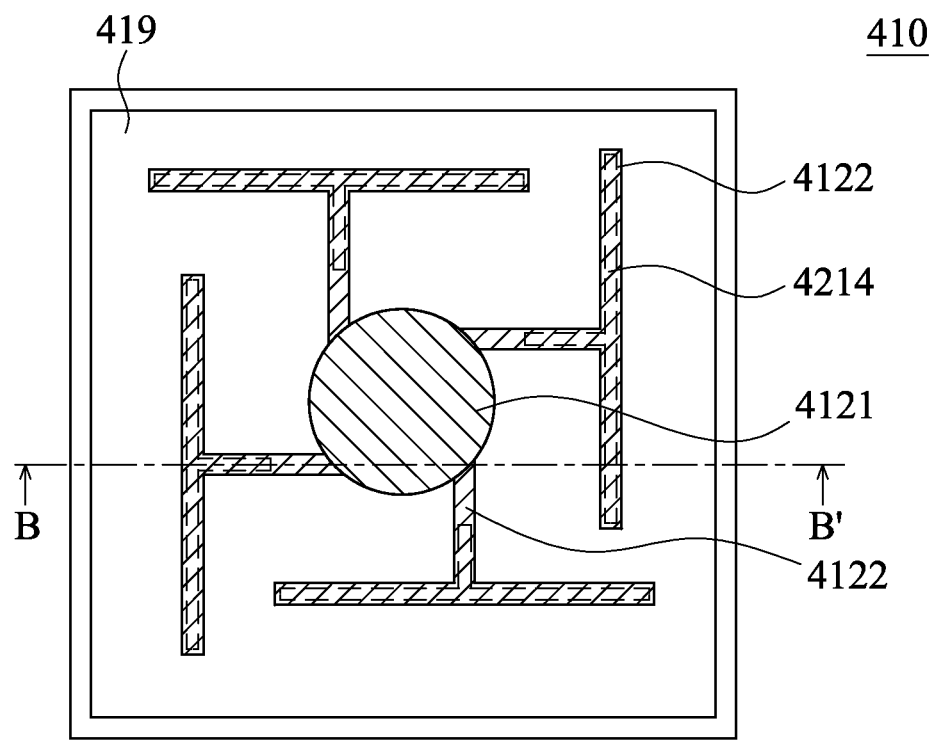
FIG. 4A shows the top view of the light-emitting unit in accordance with one embodiment of the present disclosure shown in FIG. 3F.
Figure 4B:
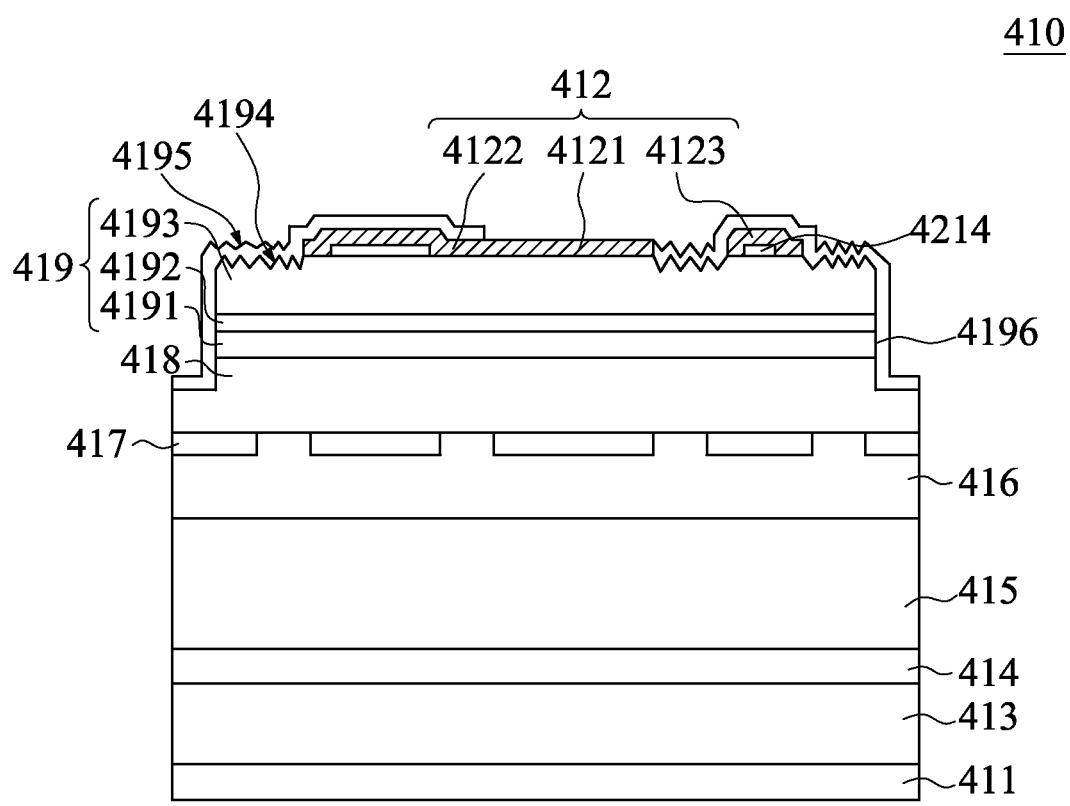
FIG. 4B shows the cross-sectional view of the light-emitting unit in accordance with one embodiment of the present disclosure shown in FIG. 4A.

FIG. 4A or 4B shows, the light-emitting unit of one embodiment of the present disclosure in accordance with FIG. 3F. FIG. 4A shows the top view of the light-emitting unit 410 to one embodiment of the present disclosure. FIG. 4B shows the cross-sectional view of the light-emitting unit 410 in FIG. 4A along the line B-B'. As FIG. 4B shows, the light-emitting unit 410 comprises a substrate 413, an adhesive layer 414 on the substrate 413, a reflective structure 415 on the adhesive layer 414, a transparent conduction structure 416 on the reflective structure 415, a window layer 418 on the transparent conduction structure 416, an insulating layer 417 between the transparent conduction structure 416 and the window layer 418, an light-emitting laminated structure 419 on the window layer 418, an electrical contacting layer 4214, a first electrode 412 on the light-emitting laminated structure 419, and a second electrode 411 below the substrate 413.

The light-emitting laminated structure 419 comprises a first conductive semiconductor layer 4191, a second conductive semiconductor layer 4193, and an active layer 4192 between the first conductive semiconductor layer 4191 and the second conductive semiconductor layer 4193. The first conductive semiconductor layer 4191 or the second conductive semiconductor layer 4193 may be, for example, a cladding layer or a confinement layer, for providing the electrons and the holes respectively to let the electrons and the holes recombine to emit a light. The first conductive semiconductor layer 4191, the active layer 4192 and the second conductive semiconductor layer 4193 may include a semiconductor material made of III-V group semiconductor material, for example, $Al_xIn_yGa_{(1-x-y)}N$ or $Al_xIn_yGa_{(1-x-y)}P$, wherein $0 \leq x, y \leq 1$; $(x+y) \leq 1$. Based on the material of the active layer 4192, the light-emitting unit 410 may emit a red light with a peak between 580 nm-780 nm, a green light with a peak between 530 nm-570 nm, or a blue light with a peak between 450 nm and 490 nm. A top surface 4194 of the second conductive semiconductor layer 4193 may be a rough surface for reducing total internal reflection, which improves the luminous efficiency of the light-emitting unit 410. A polarity of the window layer 418 may be the same with the first conductive semiconductor layer 4191.

Materials of the first electrode 412 and the second electrode 411 may be transparent conductive materials or metal materials. The transparent conductive materials comprise ITO, InO, SnO, CTO, ATO, AZO, ZTO, GZO, IWO, ZnO, AlGaAs, GaN, GaP, GaAs, GaAsP, IZO, or DLC. The metal materials comprise Al, Cr, Cu, Sn, Au, Ni, Ti, Pt, Pb, Zn, Cd, Sb, Co, or alloy that includes foregoing metal materials. The first electrode 412 connects electrically the second conductive semiconductor layer 4193. The first electrode 412 comprises an input 4121, an extending part 4122, and a protrusion structure 4123. As FIG. 4A shows, the input 4121 is approximately at the central area of the second conductive semiconductor layer 4193. The extending part 4122 extends from the input 4121 to the boundary of the light-emitting unit 410, for enhancing the current diffusion effect. As FIG. 4B shows, the protrusion structure 4123 on the electrical contacting layer 4214 can increase the ohmic contact area with the electrical contacting layer 4214, wherein the height of the protrusion structure 4123 is larger than that of the input 4121. The second electrode 411 is below the substrate 413 and connects electrically to the first conductive semiconductor layer 4191.

The electrical contacting layer 4214 is located between the extending part 4122 and the light-emitting laminated structure 419 and ohmically contacts with them. The electrical contacting layer 4214 may be made of semiconductor material, for example, Ga, Al, In, P, N, Zn, Cd, Se, or alloy that includes foregoing metal materials. A polarity of the electrical contacting layer 4214 may be the same with the second conductive semiconductor layer 4193.

The window layer 418 is transparent to the light emitted from the active layer 4192. In addition, the window layer 418 may be made of transparent conductive material, for example, ITO, InO, SnO, CTO, ATO, AZO, ZTO, GZO, IWO, ZnO, AlGaAs, GaN, GaP, GaAs, GaAsP, IZO or DLC.

As FIG. 4B shows, the maximum width of the light-emitting laminated structure 419 is smaller than the maximum width of the of the window layer 418. The window layer 418 has a top portion and a bottom portion. The top portion of the window layer 418 contacts the light-emitting laminated structure 419 and has the same width with it. The bottom portion of the window layer 418 contacts the insulating layer 417 and has a width larger than the light-emitting laminated structure 419. In other words, partial top surface of the window layer 418 is not covered by the light-emitting laminated structure 419. The outermost surface 4196 of the light-emitting laminated structure 419 is not coplanar with the outermost surface 4181 of the window layer 418. As FIG. 4A shows, from the top view drawing, the area of the light-emitting laminated structure 419 is smaller than the area of the substrate 413. The light-emitting laminated structure 419 is approximately at the central area of the light-emitting unit 410.

A passivation layer 4195 is formed along the window layer 418, side surface of the light-emitting laminated layer 419, top of the top surface 4194, and the outline of the extending part 4122 of the first electrode 412. The input 4121 of the first electrode 412 is not covered by the passivation layer 4195, in order to contact electrically with external devices. The passivation layer 4195 is on the emitting laminated structure 419 and has a rough top surface. The outline of the rough top surface is similar to the top surface 4194 and the protrusion structure 4123 of the first electrode 412. The passivation layer 4195 may be made of transparent insulating material, for example, $SiO_X$, $SiN_X$, SiON, $AlO_X$ and so on.

The transparent conduction structure 416 is transparent to the light emitted from the light-emitting laminated structure 419, and can improve the ohmic contact between the window layer 418 and reflective structure 415. In addition, the transparent conduction structure 416 and reflective structure 415 may form an omnidirectional reflector structure. The transparent conduction structure is made of the transparent material, for example, ITO, InO, SnO, CTO, ATO, AZO, ZTO, GZO, IWO, ZnO, GaP, ICO, ITiO, IZO, IGO, GAZO or a combination thereof.

The insulating layer 417 has 90% penetration coefficient to the light emitted from the light-emitting laminated structure 419. The insulating layer 417 is made of non-oxide material, for example, BCB, COC, or $SiN_X$. In one another embodiment, the insulating layer 417 may include halide, IIA group compound, or VIIA group compound, such as $CaF_2$, $CF_4$ or $MgF_2$. As FIG. 4B shows, the insulating layer 417 has a plurality of sections which is embedded into the transparent conduction structure 416 to form a plurality of top surfaces separated to each other. The topmost surface of the insulating layer 417 contacts with the window layer 418 and flushes with the topmost surface of the transparent conduction structure 416. The insulating layer 417 may be patterned for diffusing current, for example, the pattern formed at the electrical contacting layer 4214 and/or below the input 4121. In one another embodiment, the insulating layer 417 may have random pattern. The insulating layer 417 may not locate right below the electrical contacting layer 4214 and/or the input 4121. The thickness of the insulating layer 417 is less than the thickness of the transparent conduction structure 416. A plurality of bottommost surfaces of the insulating layer 417 is covered by the transparent conduction structure 416 so that the insulating layer 417 may combine with the transparent conduction structure 416 and further combine with the reflective structure 415 firmly. In one another embodiment, the insulating layer 417 has a plurality of sections which passes through the transparent conduction structure 416 and combines with the reflective structure 415 directly.

The reflective structure 415 may reflect the light emitted from the emitting laminated structure 419. The reflective structure 415 may be made of metal material, for example, Cu, Al, Sn, Au, Ag, Pb, Ti, Ni, Pt, W, or a combination thereof.

The substrate 413 may be used for supporting the light-emitting laminated structure 419 and other layers or structures. The substrate 413 is made of transparent material or conductive material. The foregoing transparent material may include, sapphire, diamond, glass, epoxy resin, quartz, acrylic acid, $Al_2O_3$, ZnO, AlN. The foregoing conductive material may include, Cu, Al, Mo, Sn, Zn, Cd, Ni, Co, DLC, graphite, carbon fiber, MMC, CMC, Si, ZnSe, GaAs, SiC, GaP, GaAsP, InP, $LiGaO_2$, or $LiAlO_2$. The adhesive layer 414 connects to the substrate 413 and the reflective structure 415. The adhesive layer 414 may be made of transparent conduction material or metal material. The foregoing transparent conduction material may include, ITO, InO, SnO, CTO, ATO, AZO, ZTO, GZO, IWO, ZnO, AlGaAs, GaN, GaP, GaAs, GaAsP, IZO, DLC, or a combination thereof. The foregoing metal material may include Cu, Al, Sn, Au, Ag, Pb, Ti, Ni, Pt, W, or a combination thereof.

Figure 5A:
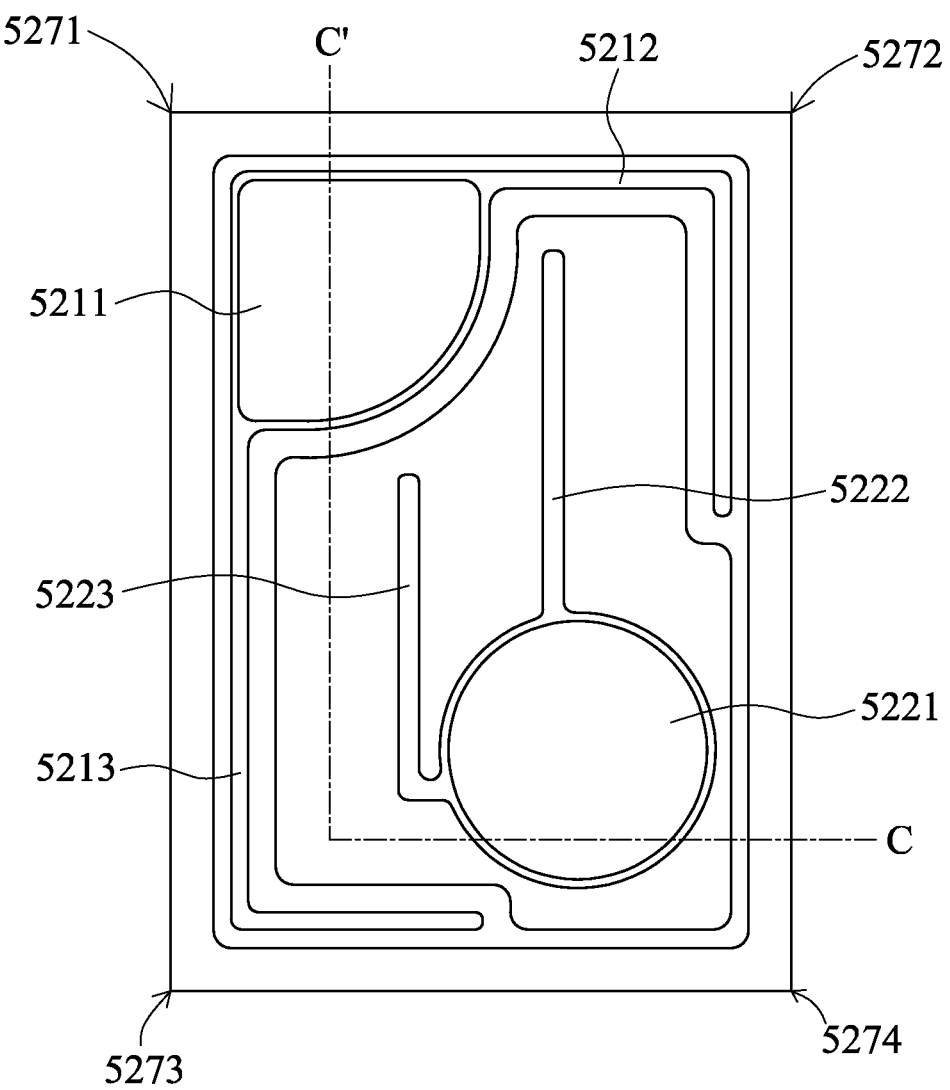
FIG. 5A shows the light-emitting unit in accordance with one embodiment of the present disclosure shown in FIG. 3G.
Figure 5B:
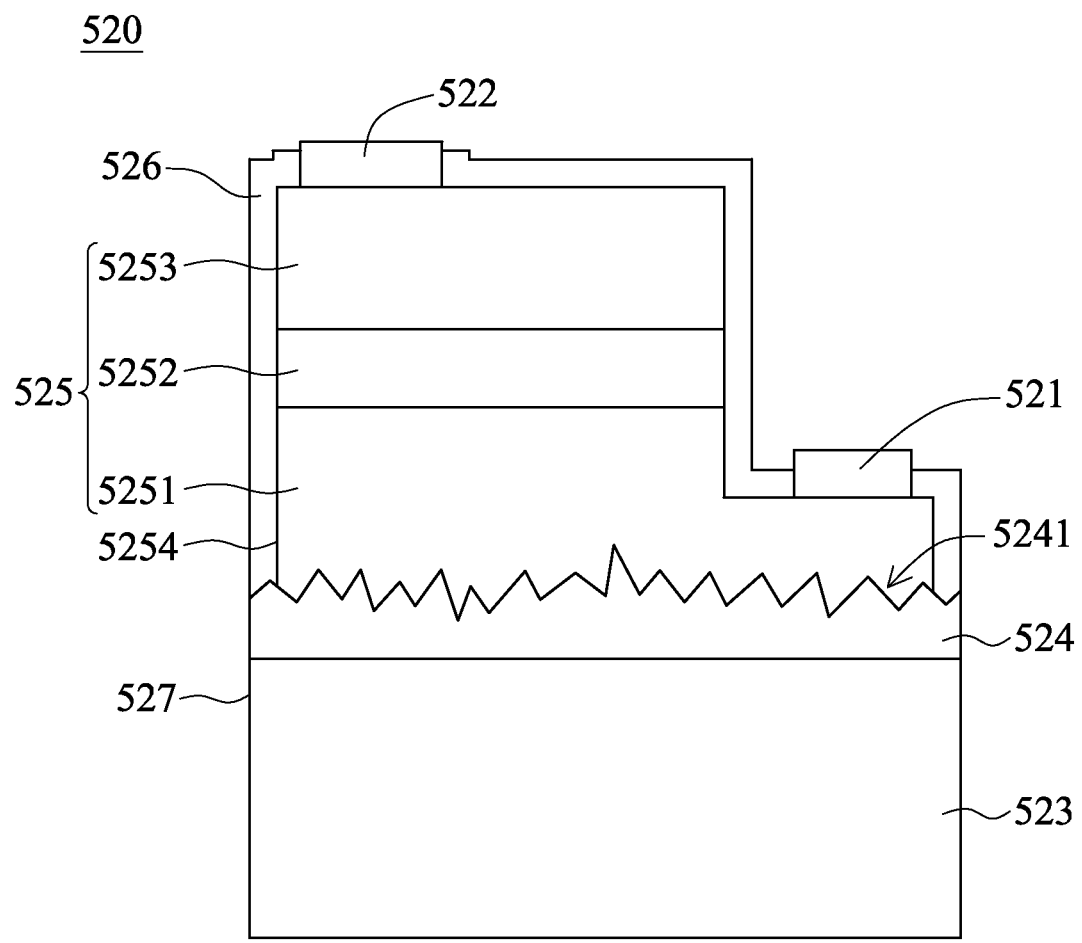
FIG. 5B shows the cross-sectional view in accordance with the light-emitting unit of one embodiment of the present disclosure shown in FIG. 5A.

FIGS. 5A and 5B show, the light-emitting unit in accordance with one embodiment of the present disclosure. FIG. 5B shows the cross-sectional view of the light-emitting unit 520 along the line C-C'. As FIG. 5B shows, the light-emitting unit 520 comprises a substrate 523, an adhesive layer 524 on the substrate 523, a light-emitting laminated layer 525 on the adhesive layer 524, and a first electrode 521 and the second electrode 522 on one side of the light-emitting laminated layer 525 opposite to the substrate 523. The light-emitting laminated layer 525 comprises a first conductive semiconductor layer 5251, a second conductive semiconductor layer 5253, and an active layer 5252 between the first conductive semiconductor layer 5251 and the second conductive semiconductor layer 5253. May refer to the paragraphs corresponding to FIGS. 4A to 4B which disclose the light-emitting laminated layer 525. May refer to the paragraphs corresponding to FIGS. 4A to 4B which disclose the substrate 523, the substrate 523 may be made of transparent material.

The adhesive layer 524 is formed on the substrate 523. The adhesive layer 524 may be made of polyimide, BCB, PFCB or indium tin oxide. The adhesive layer 524 comprises a diffusing surface 5241 having a rough surface. In other words, the first conductive semiconductor layer 5251 has the diffusing surface 5241 which connects with the adhesive layer 524. The rough surface is formed during the epitaxial process of the light-emitting unit 520, or by a wet etching or a dry etching during the die process of the light-emitting unit 520. The foregoing die process includes etching a part of the first conductive semiconductor layer 5251 by inductive coupling plasma. Accordingly, the light-emitting laminated layer 525 has rough surface attached to the substrate 523 through the adhesive layer 524. In one another embodiment, the diffusing surface 5241 of the first conductive semiconductor layer 5251 comprise a plurality of sub-protrusion structures. The first conductive semiconductor layer 5251 is further attached to the substrate 523 by the adhesive layer 524. The shape of each of the sub-protrusion structures may be hemispherical, pyramid, or diamond cone. The sub-protrusion structures make the diffusing surface 5241 have a rough surface to improve the light extraction efficiency of the light-emitting unit 520.

The paragraphs corresponding to FIGS. 4A to 4B disclose the material of the first electrode 521 and/or the second electrode 522. The first electrode 521 connects electrically with the first conductive semiconductor layer 5251. The topmost surface of the first electrode 521 is lower than that of the second conductive semiconductor layer 5253. As FIG. 5A shows, the first electrode 521 has an input 5211, and two extending parts 5212, 5213. The input 5211 is at a first corner 5271 of the light-emitting unit 520. The extending parts 5212, 5213 are extended from the input 5211 along the light-emitting unit 520, for enhancing the current diffusion effect. The extending part 5212 has a right angle located at a second corner 5272 adjacent to the first corner 5271. The extending part 5213 has a right angle located at a third corner 5273 adjacent to the first corner 5271 and diagonal to the second corner 5272. The second electrode 522 connects electrically with the second conductive semiconductor layer 5253. The topmost surface of the second electrode 522 is higher than the second conductive semiconductor layer 5253. The second electrode 522 has an input 5221, and two-extending parts 5222, 5223. As FIG. 5A shows, the input 5221 is at a fourth corner 5274 diagonal to the first corner 5271. The input 5221 of the second electrode 522 has a shape different from the input 5211 of the first electrode 521. The extending parts 5222, 5223 are extended from the input 5221 toward one side between the first corner 5271 and the second corner 5272 for enhancing the current diffusion effect. The extending parts 5222, 5223 are approximately parallel to one side between the first corner 5271 and the third corner 5273. The number of the extending parts 5222, 5223 is just an example and not limit to two.

As FIG. 5B shows, in the cross-sectional view, the maximum width of the light-emitting laminated layer 525 is smaller than the maximum width of the substrate 523 or the adhesive layer 524. In other words, a part of the topmost surface of the adhesive layer 524 is not covered by the light-emitting laminated layer 525. The outmost surface 5254 of the light-emitting laminated layer 525 is not coplanar with the outmost surface 527 of the substrate 523. As FIG. 5A shows, in the top view, the area of the light-emitting laminated layer 525 is smaller than the area of the substrate 523. The light-emitting laminated layer 525 is approximately at the central area of the light-emitting unit 520.

A passivation layer 526 is formed along the outline of the outmost surface 5254 of the light-emitting laminated layer 525, the topmost surface of the light-emitting laminated layer 525, the extending parts 5212, 5213 of the first electrode 521, and the extending parts 5222, 5223 of the second electrode 522. The input 5211 of the first electrode 521 and input 5221 of the second electrode 522 are not covered by the passivation layer 526, for connecting to external devices electrically. The passivation layer 526 is not flat since the extending parts 5212, 5213, 5222, 5223 exist. In one another embodiment, the extending parts 5212, 5213, 5222, 5223 are exposed by the passivation layer 526 which can be referred to the paragraphs corresponding to FIGS. 4A to 4B for the relative descriptions to the material of the passivation layer 526.

Figure 6A:
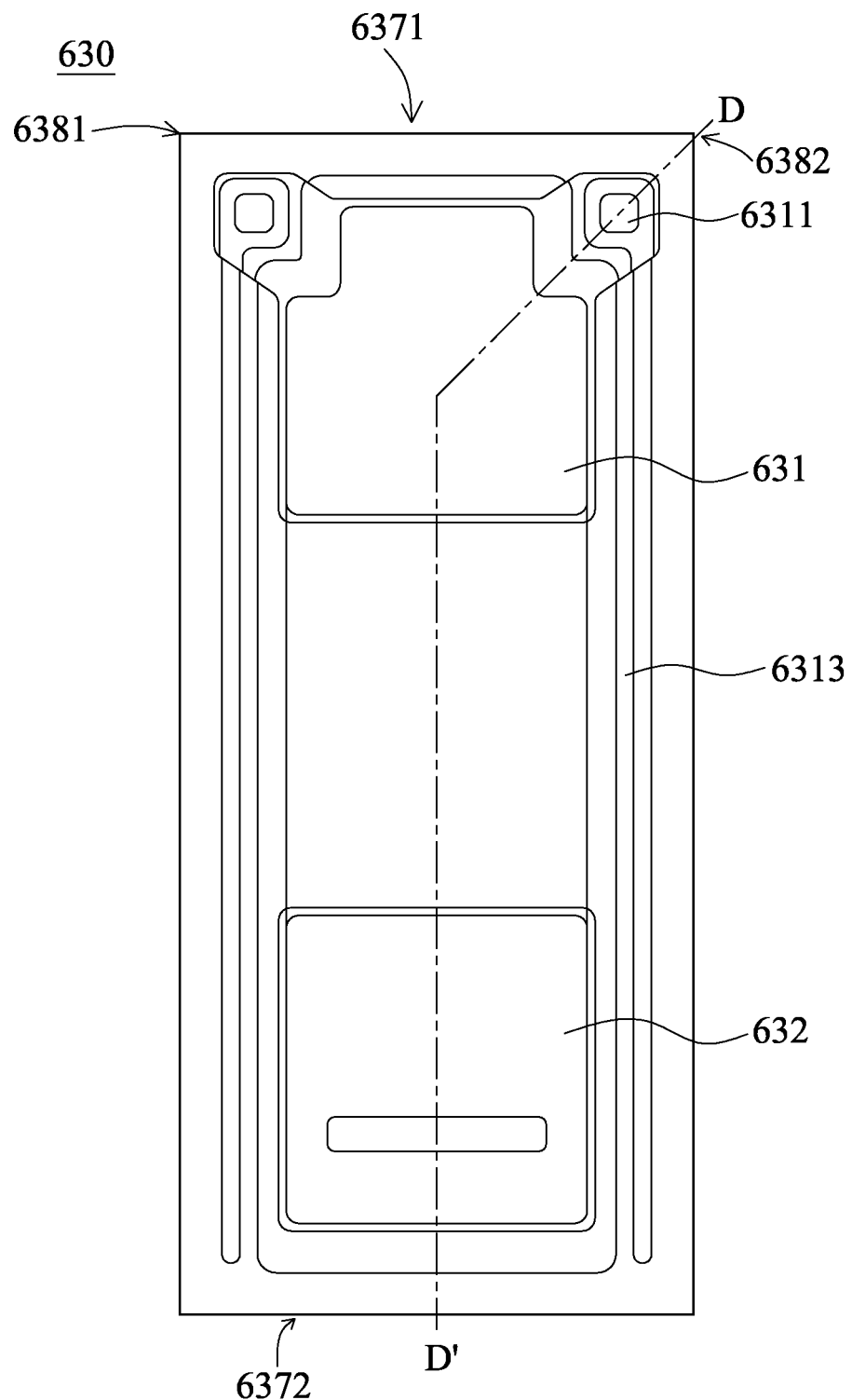
FIG. 6A shows the top view of the light-emitting unit in accordance with one another embodiment of the present disclosure.
Figure 6B:
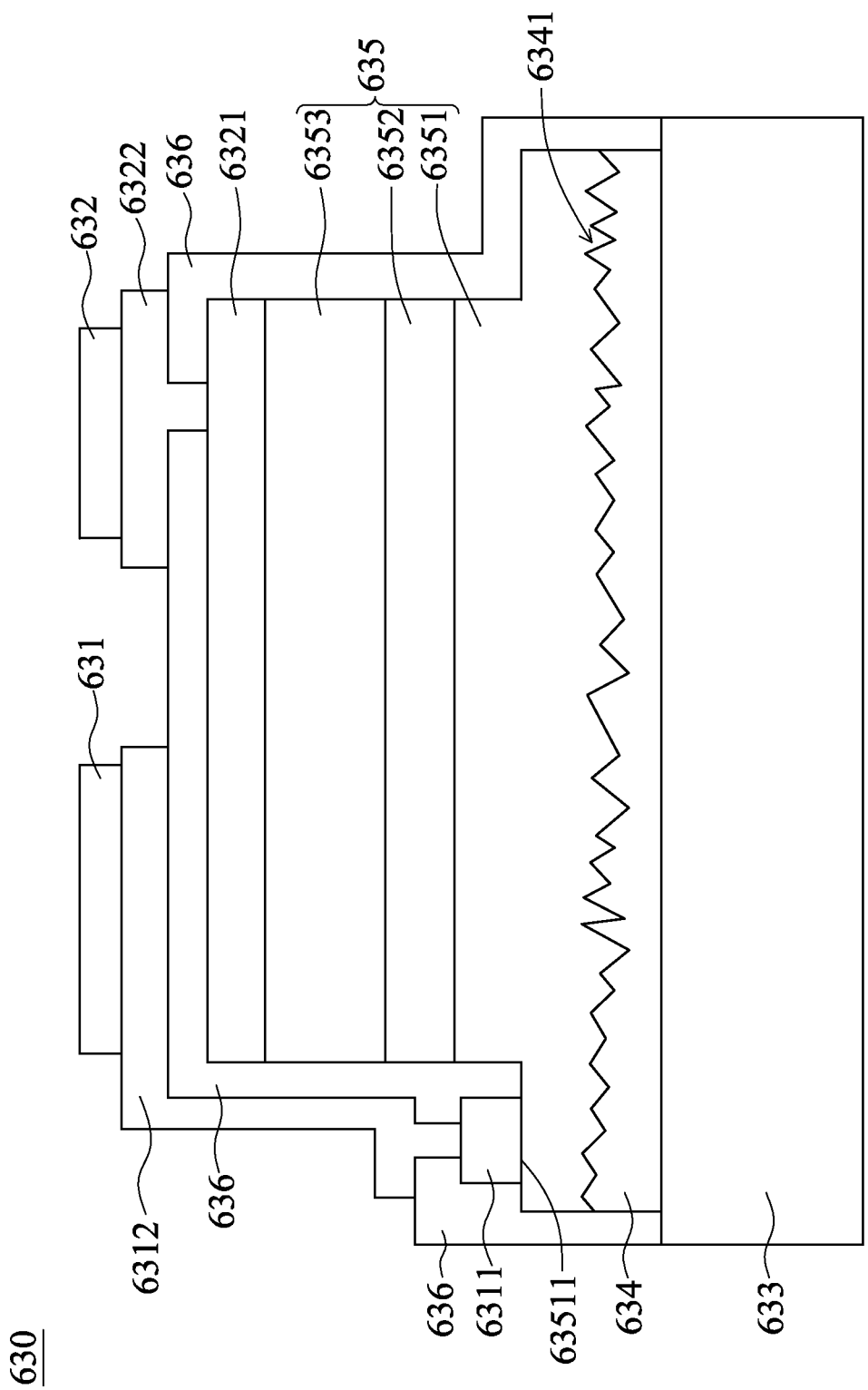
FIG. 6B shows the cross-sectional view of the light-emitting unit in accordance with one embodiment of the present disclosure shown in FIG. 6A.

FIGS. 6A-6B show that the light-emitting unit of the light-emitting device 100 in accordance with one another preferred embodiment of the present disclosure. FIG. 6A shows the top view of the light-emitting unit 630. FIG. 6B shows the cross-sectional view of the light-emitting unit 630 along the line D-D'. As the FIG. 6B shows, the light-emitting unit 630 includes a substrate 633, an adhesive layer 634 on the substrate 633, an light-emitting laminated layer 635 on the adhesive layer 634, and a first electrode 631 and a second electrode 632 on one side opposite to the substrate 633. The light-emitting laminated layer 635 comprises a first conductive semiconductor layer 6351, a second conductive semiconductor layer 6353, and an active layer 6352 between the first conductive semiconductor layer 6351 and the second conductive semiconductor layer 6353. May refer to the paragraphs corresponding to FIGS. 4A to 4B which disclose the light-emitting laminated layer 635. May refer to the paragraphs corresponding to FIGS. 4A to 4B which disclose the substrate 633. The substrate 633 may be made of transparent material. The width of the adhesive layer 634 is larger than that of the substrate 633. The adhesive layer 634 has a diffusing surface 6341 with a roughness and contacts with the light-emitting laminated layer 635. May refer to the paragraphs corresponding to FIGS. 5A to 5B which disclose the adhesive layer 634.

As FIG. 6B shows, a width of the upper portion of the light-emitting laminated layer 635 is different from the one of the lower portion of the light-emitting laminated layer 635. The upper of the light-emitting laminated layer 635 includes the second conductive semiconductor layer 6353 and the active layer 6352, and the upper portion of the first conductive semiconductor layer 6351. The lower portion of the light-emitting laminated layer 635 includes the lower portion of the first conductive semiconductor layer 6351. A width of the upper portion of the emitting laminated layer 635 is smaller than that of the lower portion of the light-emitting laminated layer 635, in a cross-sectional view of the light-emitting laminated layer 635. As a result, a top surface 63511 is not covered by the second conductive semiconductor layer 6353 and the active layer 6352. A width of the lower portion of the emitting laminated layer 635 is approximately the same as that of the adhesive layer 634.

A plurality of first electricity contacting layers 6311 are on the top surface 63511 and not covered by the first conductive semiconductor layer 6351 and contacts with the first conductive semiconductor layer 6351 electrically (only one first electricity contacting layer is shown in FIG. 6B). A second electricity contacting layer 6321 is on the top surface of the second conductive semiconductor layer 6353 and contacts with the second conductive semiconductor layer 6353 electrically. A topmost surface of the first electricity contacting layer 6311 is lower than that of a topmost surface of the second electricity contacting layer 6321. A passivation layer 636 is formed along the outline of the side surfaces of the adhesive layer 634 and the light-emitting laminated layer 635, the top surface of the first electricity contacting layer 6311, and the top surface of the second electricity contacting layer 6321. The top surfaces of the first electricity contacting layer 6311 and the second electricity contacting layer 6321 are not covered by the passivation layer 636. May refer to the paragraphs corresponding to FIGS. 4A to 4B which disclose the material of the passivation layer 636.

A first conductive connecting layer 6312 is formed along the outline of the side surface and top surface of the passivation layer 636 and extended from the first electricity contacting layer 6311. A second conductive connecting layer 6322 is extended from the second electricity contacting layer 6322 to cover the top surface of the passivation layer 636. The first conductive connecting layer 6312 is separated from the second conductive connecting layer 6322 with a distance larger than zero, which means that a part of the top surface of the passivation layer 636 is not covered by the first conductive connecting layer 6312 and the second conductive connecting layer 6322. The topmost surface of the first conductive connecting layer 6312 and the topmost surface of the second conductive connecting layer 6322 are approximately coplanar. The first electrode 631 is formed on the first conductive connecting layer 6312, and the second electrode 632 is formed on the first conductive connecting layer 6312. The first electrode 631 is separated from the second electrode 632 with a distance larger than zero. The topmost surface of the first electrode 631 and the topmost surface of the second electrode 632 are approximately coplanar. As FIG. 6B shows, above the second conductive semiconductor layer 6353, a shortest distance between the first electrode 631 and the second electrode 632 is larger than that between the first conductive connecting layer 6312 and the second conductive connecting layer 6322. The materials of the first electricity contacting layer 6311, the second electricity contacting layer 6321, the first conductive connecting layer 6312, the second conductive connecting layer 6322, and/or the first electrode 631, the second electrode 632 may be made of the metal materials. May refer to the paragraphs corresponding to FIGS. 4A to 4B which disclose the metal materials. The outmost surfaces of the first electrode 631, the first conductive connecting layer 6312, and the passivation layer 636 are not coplanar. The outmost surfaces of the second electrode 632, the second conductive connecting layer 6322, and the passivation layer 636 are not coplanar either.

As FIG. 6A shows, the first electrode 631 is located near a first end 6371 of the light-emitting unit 630, and the second electrode 632 is located near a second end 6372 opposite to the first end 6371 of the light-emitting unit 630. Each of the first electricity contacting layers 6311 is separated from each other physically, and each of the first electricity contacting layers 6311 locates near a first corner 6381 and a second corner 6382 of the first end 6371, respectively. An extending part 6313 extends from the first electricity contacting layers 6311 along the long side of the light-emitting unit 630. The extending part 6313 is covered by the light-emitting unit 630 and may be used for enhancing the current diffusion effect.

Figure 7A:
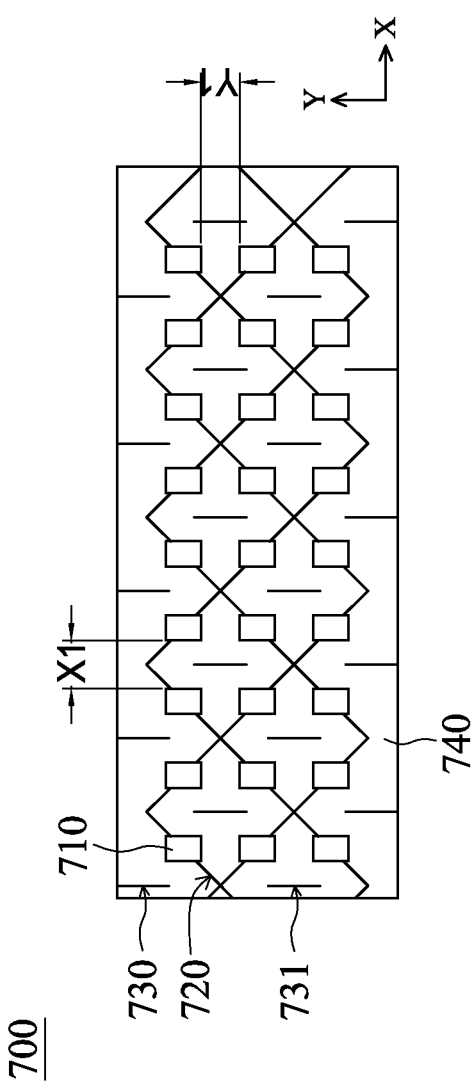
FIG. 7A shows the light-emitting device having an extendable and flexible carrier in accordance with one another embodiment of the present disclosure.

FIG. 7A shows another embodiment of the light-emitting device 700 having an extendable and flexible carrier. The light-emitting device 700 comprises a flexible carrier 740. A plurality of light-emitting units 710 is set on the flexible carrier 740 and arranged as an array, which means that the light-emitting units 710 in FIG. 7A are arranged regularly both in an X direction and a Y direction. Two adjacent light-emitting units 710 are spaced with a length X1 in the X direction, and with a length Y1 in the Y direction. A connecting wire 720 is set on flexible carrier 740 to connect the light-emitting units 710 to each other and to connect electrically to other electronic devices (not shown in FIG. 7). The ways to connect the light-emitting units 710 to each other are described as follows: in one embodiment, two adjacent light-emitting units 710 in the same row are in series connection to each other, also two adjacent light-emitting units 710 in the same line and different row are in parallel connection to each other. The foregoing four light-emitting units 710 form an array unit. The other light-emitting units 710 are arranged and expanded based on the way of the array unit in an X direction and a Y direction. Different array units are in series connection to each other, whether in an X direction or a Y direction. In one another embodiment (not shown in FIG. 7), the light-emitting units 710 in the same row are all in series connection to each other, but the light-emitting units 710 in one row are in parallel connection to the ones in the adjacent row. The flexible carrier 740 further comprises a plurality of segmentations 730, 731. The segmentations 730, 731 are arranged based on the same way of the array unit, wherein one end of each of the segmentations 730 is at the boundary of the flexible carrier 740, and the other end of each of the segmentations 730 is within the flexible carrier 740. Two ends of the segmentation 731 are both within the flexible carrier 740. Before the light-emitting device 700 is extended, the flexible carrier 740 has a continuous coplanar surface, which means that two sides of the segmentations 730 are close to each other, as well as two sides of the segmentations 731 are close to each other.

Figure 7B:
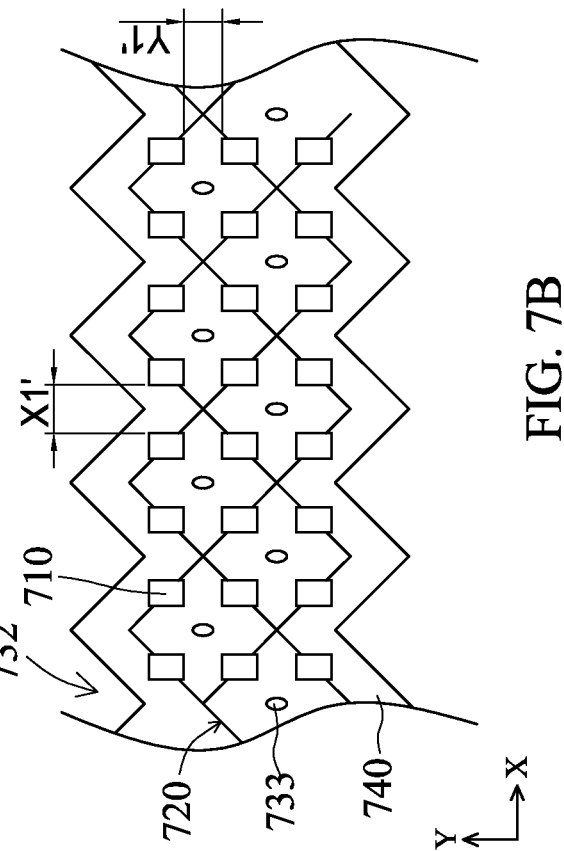
FIG. 7B shows the top view of the light-emitting device in FIG. 7A after being extended.

FIG. 7B shows the top view of the light-emitting device 700 in FIG. 7A after being extended. When the light-emitting device 700 is extended, as FIG. 7B shows, the light-emitting device 700 is extended along an X direction. After being extended, two adjacent the light-emitting units 710 in the X direction are spaced with a length X1', the length X1' is larger than the original length X1. The light-emitting device 700 is extended along a Y direction. After being extended, two adjacent the light-emitting units 700 in the Y direction are spaced with a length Y1', the length Y1' is larger than the original length Y1. The light-emitting device 700 is extended along the X direction and Y direction at the same time. The foregoing X direction and Y direction are vertically to each other. A plurality of gaps 732 is formed at the boundary of the flexible carrier 740, and a plurality of closing gaps 733 is formed inside the flexible carrier 740. In that case, the flexible carrier 740 may not have a continuous coplanar surface, which means that the flexible carrier 740 is not a structure with a single plane anymore, but becomes a structure with multiple blocks located on different planes.

Figure 8:
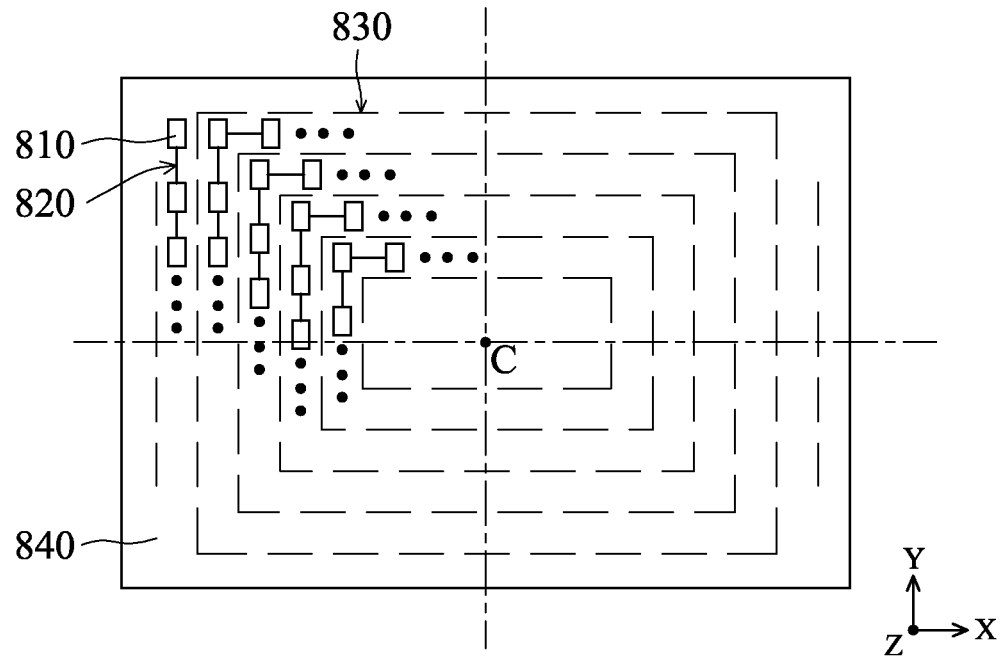
FIG. 8 shows the top view of the light-emitting device having an extendable and flexible carrier in accordance with one another embodiment of the present disclosure.

FIG. 8 shows the top view of the light-emitting device 800 having an extendable and flexible carrier in accordance with another embodiment of present disclosure. A plurality of light-emitting units 810 is on the flexible carrier 840. A connecting wire 820 is set on the flexible carrier 840 to connect the light-emitting units 810 to each other and other external electrical devices (not shown in FIG. 8). A plurality of light-emitting units 810 is arranged on the flexible carrier 840 in a concentric circles arrangement or an approximate concentric circles arrangement. The light-emitting units 810 at the same circle are connected to each other in series through the connecting wire 820, and the light-emitting units 810 at different circles are connected to each other in parallel through an another connecting wire (not shown in FIG. 8). In another embodiment, all light-emitting units 810 arranged on the flexible carrier 840 in a concentric circles arrangement or an approximate concentric circles arrangement may connect to each other in series through a wire on the surface of the flexible carrier 840. The light-emitting units 810 be connected in series connection starting from the outmost circle to the innermost circle, then connect to other external electrical devices through one another wire on another surface of the flexible carrier 840 (not shown in FIG. 8). The flexible carrier 840 further comprises a plurality of segmentations 830. The segmentations 830 are arranged as a nested structure within the flexible carrier 840. More specifically, the segmentations 830 are arranged as up-down and left-right lateral symmetry based on the center C of the flexible carrier 840. Before the light-emitting device 800 is extended, the flexible carrier 840 has a continuous coplanar surface, which means that two sides of the segmentations 830 are close to each other. When the light-emitting device 800 is extended (not shown in FIG. 8), the light-emitting device 800 is extended along a Z direction vertical to the surface of the light-emitting device 800, or the light-emitting device 800 is extended along an X direction, a Y direction, and a Z direction at the same time. The foregoing X direction, Y direction, and Z direction form a Cartesian coordinates. At this time, a plurality of closing gaps is formed inside the flexible carrier 840 (not shown in FIG. 8), and the flexible carrier 840 does not have a continuous coplanar surface anymore, which means that the flexible carrier 840 becomes a structure with a single plane to an another structure with multiple blocks located on different planes. More specifically, the flexible carrier 840 is extended from a plane to a cone (not shown in FIG. 8).

Figure 9:
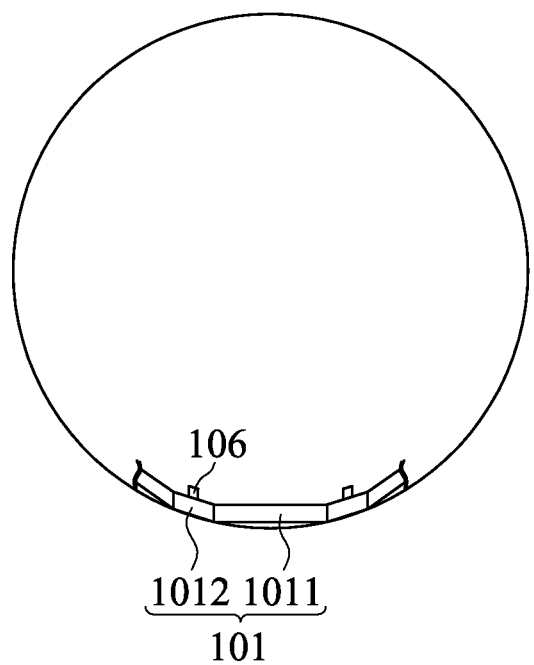
FIG. 9 shows the light-emitting device having an extendable and flexible carrier being placed in an extendable container.

As FIG. 9 shows, the light-emitting device 100 having an extendable and flexible carrier is placed in an extendable container 900, for example, a balloon. The material of the balloon is for example a rubber, emulsion, or PE. The carrier part 1012 of the flexible carrier 101 is attached directly to the inner surface of the balloon. The extendable part 101 is not attached directly to the inner surface of the balloon. The flexible carrier 101 which carries the light-emitting unit 106 may be extended along with the amount of the gas in the balloon 900. Since the distance between the light-emitting unit 106 and the inner surface of the balloon 900 is not changed along with the balloon 900 after being extended, the light intensity of the surface of the balloon 900 may be maintained in a stable value. The light intensity of the surface of the balloon 900 may be uniform by being coupled with the arrangement of the light-emitting units 106 on the inner surface of the balloon 900. In another embodiment, the light-emitting device 700 may be set within the balloon 900 (not shown in FIG. 9). In another embodiment, the light-emitting device 800 may be set within the balloon 900 (not showed in FIG. 9), for example, may set the light-emitting device 100, 700, or 800 within the balloon 900 to apply to the photodynamic therapy equipment for curing diseases such as cancer.

Figure 10:
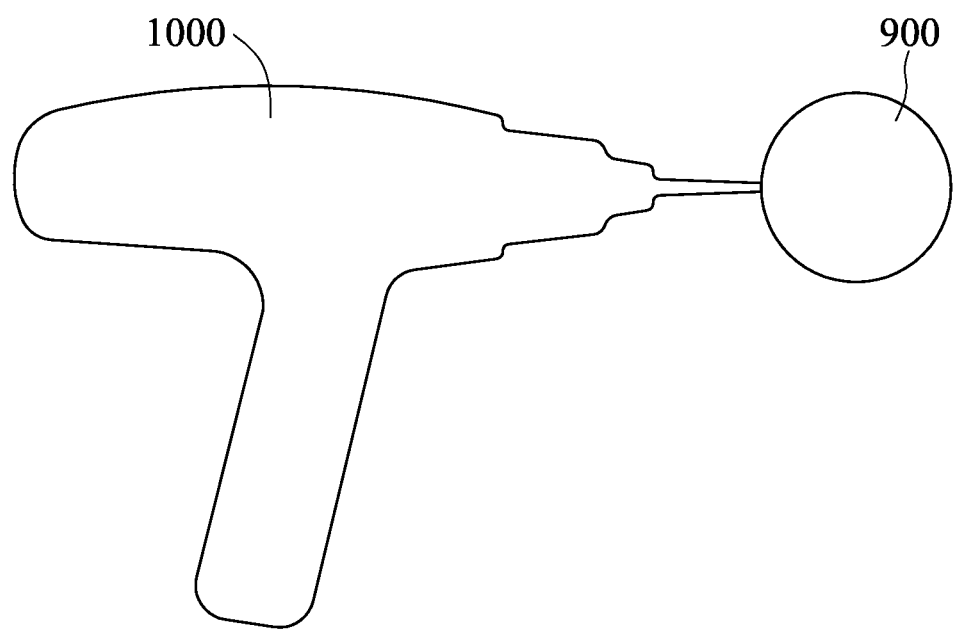
FIG. 10 shows one photodynamic therapy equipment with a balloon having the light-emitting device of the present disclosure.

FIG. 10 shows one photodynamic therapy equipment. The balloon 900 shown in FIG. 9 is applied to the photodynamic therapy equipment 1000. The inner of the oral cavity may be lighted by blowing the balloon 900, which results in reducing the discomfort caused by opening the oral cavity for a long period of time. Still, the curing effect is significant by means of the better and more uniform of the light intensity.

The present disclosure has been described with some embodiments thereof and it is understood that many changes and modifications in the described embodiments can be carried out without departing from the scope and the spirit of the disclosure that is intended to be limited only by the appended claims.

What is claimed is:
1. A light-emitting device, comprising:
  a flexible carrier having a continuous common surface;
  a light-emitting unit set on the flexible carrier;
  a plurality of segmentations formed within the flexible carrier; and
  a connecting wire set on the flexible carrier,
  wherein the flexible carrier has a plurality of non-coplanar blocks after being extended, wherein the flexible carrier after being extended has a length larger than that of the flexible carrier before being extended, wherein the flexible carrier comprises a first sub-carrier and a second sub-carrier respectively formed at two sides of one of the plurality of segmentations, and wherein the flexible carrier, after being extended, has a gap formed between the first sub-carrier and the second sub-carrier.

2. The light-emitting device as claimed in claim 1, wherein the flexible carrier has a carrier part; and an extendable part, the light-emitting unit is set on the carrier part, and the extendable part has the continuous common surface.

3. The light-emitting device as claimed in claim 2, wherein the extendable part has the plurality of segmentations configured to be stretched and expended for forming a plurality of sub-carriers.

4. The light-emitting device as claimed in claim 3, wherein when the flexible carrier is not extended, the plurality of sub-carriers is located on a single plane, when the flexible carrier is extended, the plurality of sub-carriers is located on different planes.

5. The light-emitting device as claimed in claim 1, wherein the connecting wire is a curved structure.

6. The light-emitting device as claimed in claim 1, wherein one part of the plurality of the segmentations is at the boundary of the flexible carrier and another part of the plurality of the segmentations is within the flexible carrier.

7. The light-emitting device as claimed in claim 1, wherein the plurality of segmentations is arranged in up-down and left-right lateral symmetry based on a center of the flexible carrier.

8. The light-emitting device as claimed in claim 1, wherein the light-emitting device is extended along a first direction and a second direction, and the first direction and the second direction are vertical to each other.

9. The light-emitting device as claimed in claim 1, wherein the light-emitting device is extended along a first direction, a second direction and a third direction, and the first direction, the second direction, and the third direction form a Cartesian coordinates.

10. The light-emitting device as claimed in claim 1, wherein light-emitting device comprises a plurality of light-emitting units set on the flexible carrier and arranged as an array.

11. The light-emitting device as claimed in claim 1, wherein light-emitting device comprises a plurality of light-emitting units set on the flexible carrier and arranged as an array arrangement.

12. The light-emitting device as claimed in claim 11, wherein the flexible carrier further comprises a plurality of segmentations set on the flexible carrier and arranged as an array arrangement.

13. The light-emitting device as claimed in claim 12, wherein one end of each of the plurality of segmentations is at a boundary of the flexible carrier, the other end of each of the plurality of segmentations is within the flexible carrier.

14. The light-emitting device as claimed in claim 1, further comprising a plurality of light-emitting units set on the flexible carrier and arranged as a concentric circle arrangement.

15. The light-emitting device as claimed in claim 14, wherein the plurality of segmentations is set on the flexible carrier and arranged as nested structure within the flexible carrier.

16. The light-emitting device as claimed in claim 15, wherein the plurality of segmentations is arranged as up-down and left-right lateral symmetry based a center of the flexible carrier.

17. A device, comprising:

a main body; and a light-emitting device set within the main body, including:

a flexible carrier having a continuous common surface;

a light-emitting unit set on the flexible carrier;

a plurality of segmentations formed within the flexible carrier; and a connecting wire set on the flexible carrier, wherein when the flexible carrier is extended, the flexible carrier has a plurality of blocks not coplanar to each other, wherein the flexible carrier after being extended has a length larger than that of the flexible carrier before being extended, wherein the flexible carrier comprises a first sub-carrier and a second sub-carrier respectively formed at two sides of one of the plurality of segmentations, and wherein the flexible carrier, after being extended, has a gap formed between the first sub-carrier and the second sub-carrier.

18. The device as claimed in claim 17, wherein the main body is a balloon.

19. The device as claimed in claim 18, wherein the balloon is used in a photodynamic therapy equipment.

\* \* \* \* \*